United States Patent [19]

Mikkelsen

[11] Plant 5,134

[45] Nov. 8, 1983

[54] IMPATIENS PLANT

[75] Inventor: James C. Mikkelsen, Ashtabula, Ohio

[73] Assignee: Mikkelsens, Inc., Ashtabula, Ohio

[21] Appl. No.: 354,043

[22] Filed: Mar. 2, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

An impatiens plant known by the cultivar name Gemini, and characterized by its clear bright pink flower color and contrasting dark green variegated foliage; highly floriferous habit; firm petal texture; relatively large flowers, with distinct deep pink to red throat; continuous flowering and highly stable flower color, with little fading in summer, and by its semi-procumbent and weather resistant habits which make it ideal for baskets and bedding plants.

1 Drawing Figure

1

The present invention relates to a new and distinctive cultivar of Impatiens plant botanically known as Impatiens, and known by the cultivar name Twinkles. The new cultivar was developed by me through controlled breeding in Ashtabula, Ohio. The seed parent was Trapeze, a cultivar developed by Longwood Gardens, and the pollen parent was 77-755-3 (Mikkelsens). Asexual reproduction of terminal or stem cuttings has shown that the unique features of this new impatiens are stabilized and are reproduced true to type in successive propagations.

The following characteristics distinguish Twinkles from both its parent varieties and other cultivated impatiens of this type known and used in the floriculture industry:

1. Self-branching, procumbent growth which appears somewhat fragile but has withstood heavy winds and rain. Ideal growth for hanging baskets but not upright enough for pot culture. Very useful for bedding plants.

2. Very floriferous because of high bud count in leaf whorl, and many growing points due to excellent self-branching. The new cultivar flowers very quickly from cuttings and continues to flower outside until destroyed by a killing frost.

3. The flower color is a sharp clear pink in cool regimes of spring and fall, but salmon pink in middle of summer. Color as illustrated is more distinct than Trapeze or the cultivar Telstar, disclosed in U.S. Plant Pat. No. 4,733.

4. Flower color is similar to Columbia under low light regimes, but Twinkles changes to salmon pink whereas Columbia fades slightly to a lighter tone of its defined color. Flowers of Twinkles are smaller than Columbia. Columbia is disclosed in a pending application of applicant.

5. Twinkles is a faster growing, freer breaking, fuller and larger plant with less vigorous stems than Columbia.

6. The foliage of Twinkles has greater variegation and is narrower and longer than the foliage of Columbia. The foliage of Twinkles appears lighter in summer, because variegation increases, but the basic green color in the foliage is similar to Columbia.

7. Self-branching of Twinkles is similar to branching in Telstar but rate of growth of Twinkles is faster than Telstar.

2

8. Twinkles and Cosmos are very similar in all aspects excepting flower color, which in Cosmos is an intense mauve. Cosmos is also disclosed in a pending application of applicant.

9. Unlike Sultana impatiens, Mikkelsen cultivars of New Guinea Impatiens hybrids require high light and ample nutrition for maximum expression of their characteristics.

The accompanying colored photograph taken in late September outdoors illustrates the overall appearance of Twinkles. The photo is a generally top perspective view of the plant and shows the colors as true as it is reasonably possible to obtain in a colored reproduction of this type.

The following is a detailed description of my new impatiens cultivar based on plants produced under commercial practices in Ashtabula, Ohio. The illustrated specimen was planted outside during the first week of June from a 4" pot. By the middle of September, the plant measured 60 cm. diameter × 30 cm. high. Flowering continued until killing frost in early November. Color references are made to The Royal Horticultural Society Colour Chart except where general terms of ordinary dictionary significance are used.

Parentage: Trapeze (Longwood Gardens) crossed with Mikkelsen seedling 77-755-3.

Propagation:

(A) *Stem cuttings.*—Cuttings 15 mm. long will develop to 4–5 cm. in 21–28 days.

(B) *Time to initiate root.*—8–10 days at 23° C. summer.

*Time to initiate root.*—12–14 days at 20° C. winter.

(C) *Rooting habit.*—Very fibrous, dendritic, abundant.

Plant Description:

(A) *Form.*—A relatively low, self-branching, full, semi-procumbent flowering herb with ligh red to pink stems.

(B) *Habit of growth.*—Fast growing, medium internodes, semi-procumbent, or spreading, self-branching growth habit.

(C) *Foliage.*—Leaves simple, opposite on vegetative shoots but developing into a whorl when flowering initiates; numbering 6–7. (1) Size: 7–8 cm. long by 2.5–3 cm. wide; under stress leaves become narrow, approaching 8–8.5 cm. long by 2–2.5 cm. wide. (2) Shape: lanceolate, apex acuminate, base acute, highly variegated; young leaves tend to be concave. (3) Texture: top side rugose, underside glabrous. (4) Margin: nearly entire to finely serrated. (5) Color: young foliage, top side yellow green 146-A; under side yellow green 147-B-C; mature foliage, top side green 137-A; under side green 137-B-C. Foliage highly variegated in mid-summer. (6) Venation: pinnate.

Flowering description:

(A) *Flowering habits.*—Flowers are initiated in whorls of 6–7 leaves, usually one flower per leaf. Flowers open in successive stages around the whorl, with the last several blooms still flowering as the first flower in the next whorl begins to open.

(B) *Natural flowering season.*—Flowering is indeterminate and continuous all year around, with the amount and time of flowering depending on quantity of light.

(C) *Flower buds.*—Ellipsoidal with deep pink to light red spur having a hollow throat and originating from the major sepal behind the ovary; flowers perfect.

(D) *Flowers borne.*—On individual deep pink pedicels originating from the whorl of leaves.

(E) *Quantity of flowers.*—Because of self-branching which develops many growing points, plants appear to be highly floriferous but there are usually only 6–7 flowers per whorl of leaves.

(F) *Petals.*—(1) Shape: Top petal separated and dominant, lower four heart-shaped, overlapping, middle two smallest. (2) Color: top side in spring/fall when opening, red purple 62A-B, fading to 62B-C; underside 62-D/63-D; top side when opening in summer full light, 38-A. (3) Number of petals: five (5). (4) Size of flowers: to 5 cm. diameter spring/fall; approximately 4 cm. under stress in summer.

(G) *Reproductive organs.*—(1) Stamens: five (5) in number. a. Anther shape: hooded, color light pink to white. b. Pollen color: white. (2) Pistils: a. Stigma: five (5), segmented column shaped; colorless. b. Style: colorless. c. Ovaries: five (5) in number, celled, size 3.5–4 mm., color green. Capsule explosively dehiscent.

Disease resistance: No evidence to date of susceptibility to major disease or insect problems.

I claim:

1. A new and distinct cultivar of impatiens known by the cultivar name Twinkles, as described and illustrated, and particularly characterized by its sharp clear pink flower color in cool regimes and generally salmon pink flower color in mid-summer; variegated foliage; excellent self-branching and procumbent growth habits; high floriferousness, and quick flowering; fast growing and free breaking, providing full and large plant, and by its relatively small flowers.

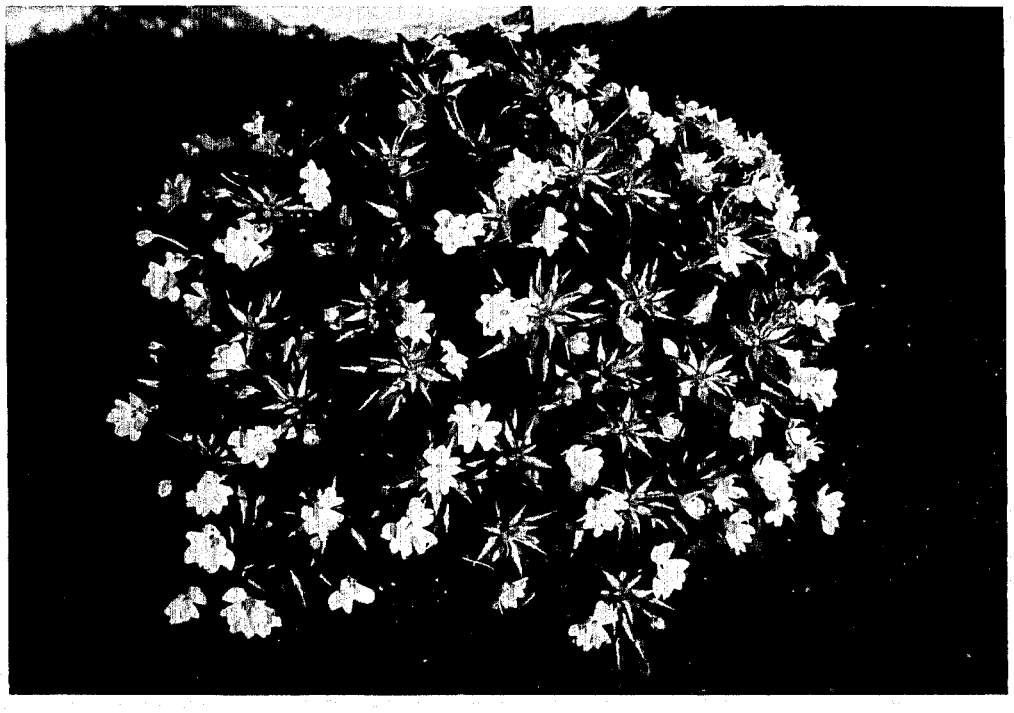

* * * * *